Figure 3:
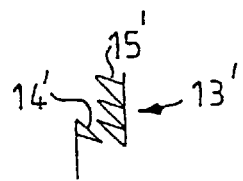

United States Patent [19]
Bergstrom

[11] Patent Number: 6,066,159
[45] Date of Patent: May 23, 2000

[54] SURGICAL INSTRUMENT

[76] Inventor: Bo Bergstrom, Kristinebergsgatan 11, S-792 34 Mora, Sweden

[21] Appl. No.: 09/077,527
[22] PCT Filed: Nov. 28, 1996
[86] PCT No.: PCT/SE96/01560
  § 371 Date: May 29, 1998
  § 102(e) Date: May 29, 1998
[87] PCT Pub. No.: WO97/20508
  PCT Pub. Date: Jun. 12, 1997
[51] Int. Cl.[7] .................................................. A61B 17/28
[52] U.S. Cl. ........................... 606/208; 605/151; 605/207
[58] Field of Search ................................... 606/151, 157, 606/205, 208, 207

[56] References Cited

U.S. PATENT DOCUMENTS 5,275,624  1/1994  Haber et al. .............................. 606/208
5,304,183  4/1994  Gourlay et al. .
5,514,147  5/1996  Hoskin et al. ........................... 606/208

FOREIGN PATENT DOCUMENTS

WO 95/11620  5/1995  WIPO .

Primary Examiner—Gary Jackson
Attorney, Agent, or Firm—Young & Thompson

[57] ABSTRACT

The invention relates to a surgical instrument, comprising two legs (2, 3) pivotably joined to each other by means of a joint (4), which legs on the first side of the joint (4) have gripping surfaces (5) facing towards each other and on the other side of the joint are equipped each with a handgrip (6) and locking means (13, 13'), by means of which the legs (2, 3) are lockable with each other, characterized in that the handgrips (6) by means of coupling means (10) are removably connected with the respective leg (2, 3).

9 Claims, 2 Drawing Sheets

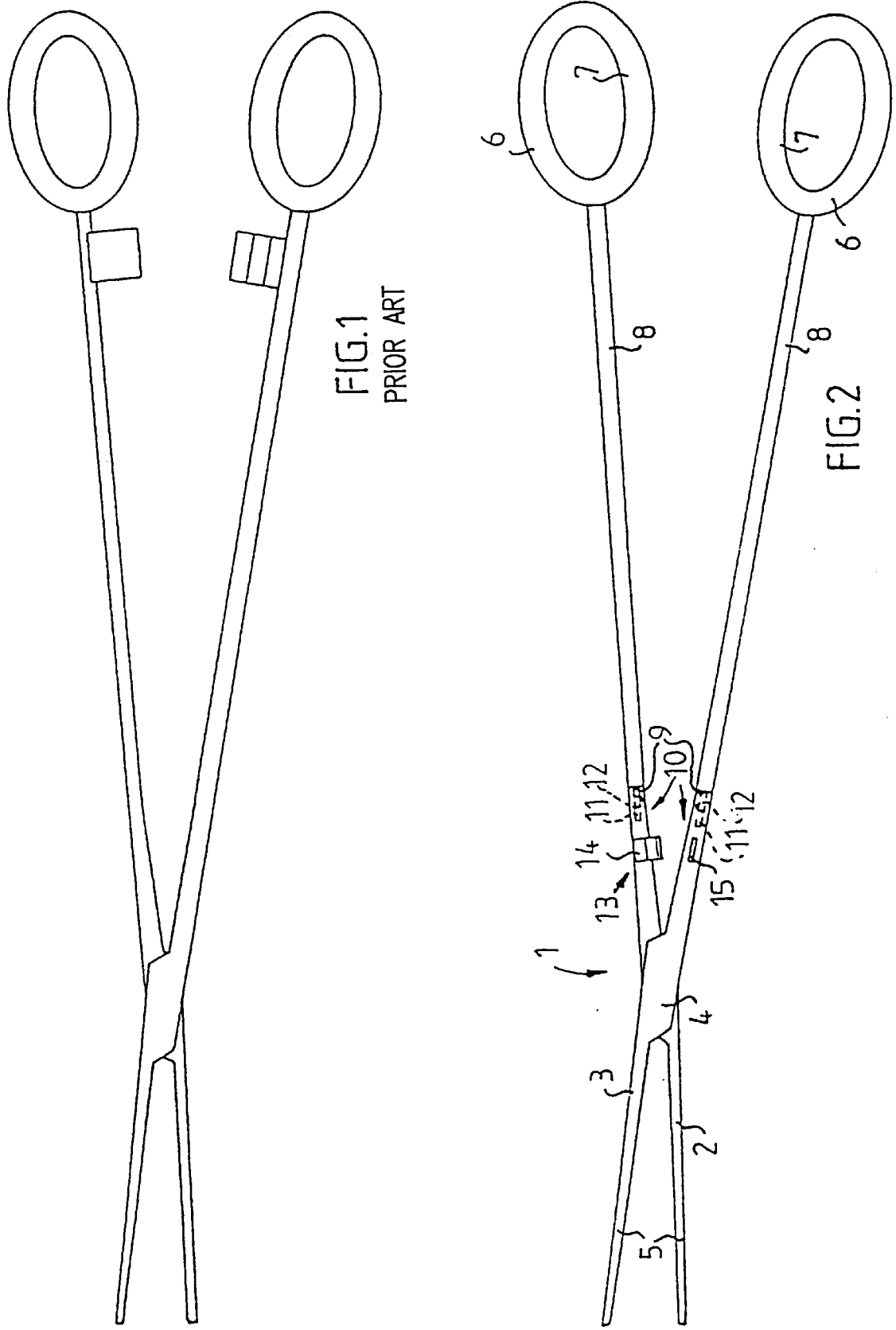

SURGICAL INSTRUMENT

The present invention relates to a surgical instrument comprising two legs pivotably joined with each other by means of a joint, which legs on a first side of the joint have gripping surfaces directed towards each other and on the other side of the joint are equipped each with a handgrip and locking means by means of which the legs are lockable with each other.

Developments in surgery tend towards less invasive methods. Instead of so-called open abdominal surgery where the abdomen is opened through a large cut in the abdominal wall, laparoscopy, which is generally known as key-hole surgery is used. In a special form of laparoscopy, called gas-laparoscopy, a space for the inspection and instrumentation is formed through the abdomen being expanded with carbon dioxide gas. An opening with a size of about 5–15 mm is made in the wall of the abdomen and gastight inlet ports, also known as trocars, are arranged in the opening. Specially manufactured instruments which have a round cross-section can enter the abdomen through the trocars. An optical instrument such as an laparoscope can be present among these instruments.

As during gas laparoscopy the trocars and instruments together must make a gastight seal, expensive, specially manufactured (but in many cases inadequate instruments) are required. Furthermore, the gas pressure forms a load on the circulatory system of the body which comprises the heart and blood vessels and there is a risk of leakage of the gas to the blood.

In order to avoid these problems, so-called gasless laparoscopy can be performed. A space for inspection and instrumentation is formed through the front abdominal wall being lifted upwards with the help of a mechanical arrangement. The gasless technique means that surgical instruments of varying sizes, which are found in abundance in every central operation room, can be introduced down through the abdominal wall. These instruments with differently shaped shafts can be inserted into the abdomen without the use of trocars.

Hemostatic forceps are instruments with flattened jaws which can surround a large or a small volume of tissues and with a powerful grip hold them collected with no flow of blood until it is desired to release the tissue alternatively knot them together with a thread. The instrument belongs to one of the most used during general abdominal surgery and one or more of such hemostatic forceps can nearly always be found in every operation. Hemostatic forceps are a favorite instrument among surgeons and are difficult to replace with other known clamps of various constructions which are used to grip a small volume of tissue. The usability of the hemostatic forceps depends on its construction with two legs equipped with loops which are held together with a joint and which can be easily manipulated. The jaws of the hemostatic forceps can be closed with a large force and locked in the closed position by means of a locking means. The large closing force is achieved by the joint being positioned in a direction towards the jaws. In this way the length of the part of the respective leg, called the shaft, which is situated between the joint and the respective loops, is large which means that a large torque can be achieved around the joint when the respective loops are moved in a direction towards each other by means of hand force. Such a hemostatic forceps according to the known art is shown in FIG. 1 of the appended drawing. Clamps of different constructions intended to replace hemostatic forceps do not have the same force in closure.

In gasless laparoscopy surgery such a known hemostatic forceps can be used but the shaft of the hemostatic forceps blocks the inlet opening used in the body in the continued gasless technique and furthermore makes it impossible to shift to the gas technique because the shaft has an irregular shape which does not permit the use of a gastight inlet port.

The object of the present invention is to produce a surgical instrument which can be used in both gasless laparoscopy and gas laparoscopy without blocking the inlet opening used in the body.

According to the invention this object is achieved with a surgical instrument in which the handgrips by means of coupling means are removably connected with the respective legs.

With such a surgical instrument the shaft can be removed from the legs and the heldtogether part left inside the body. No part of the instrument retained in the body thereby penetrates the surface of the body, whereby the inlet opening used is not blocked during continued use of the gasless technique, and a shift can be made to the gas technique, if so desired. The instrument part left inside can be taken out later.

Figure 4:
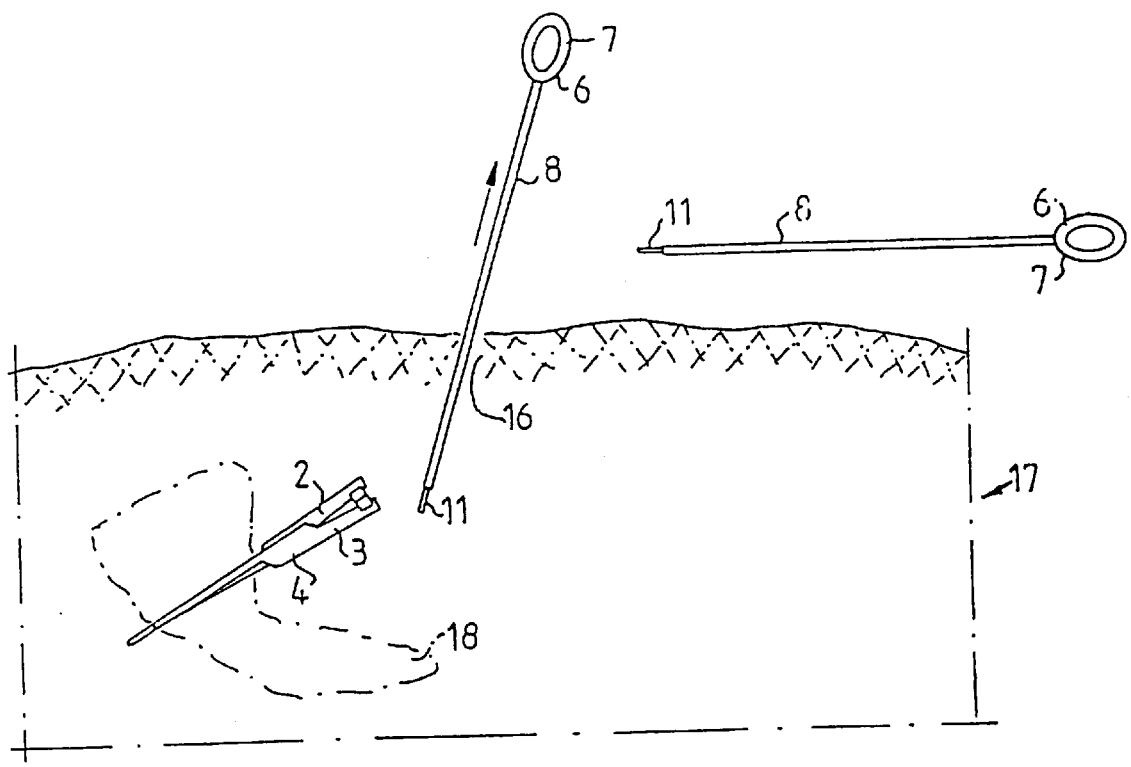

The invention will be described more closely with reference to the embodiment examples shown on the appended drawing, where:

FIG. 1 shows a surgical instrument which forms a hemostatic forceps of known type, FIG. 2 shows a surgical instrument according to the present invention, FIG. 3 shows a second embodiment of a locking means, and FIG. 4 shows how the surgical instrument is used.

FIG. 1 relates to a surgical instrument in the form of a hemostatic forceps according to the prior art which has been described in more detail in the introduction of the description.

FIG. 2 relates to a surgical instrument 1 according to the present invention. The instrument 1 has two legs 2,3 which are pivotably joined with each other via a joint 4. The joint 4 can, for example, be formed of a pin (not shown), which is introduced into a bore in respective legs 2,3. On a first side of the joint 4 the legs 23 have gripping surfaces 5 which are facing towards each other. The gripping surfaces 5 can be flat and equipped with corrugations in order to provide a firmer grip of the organ or the tissue which is to be gripped with the instrument 1. The legs 2,3 on the first side of the joint form jaws.

On a second side of the joint 4 the legs 2,3 are equipped with a handgrip 6 in the form of a loop 7 arranged on the respective leg, into which a finger can be introduced. The respective loop 7 is equipped with a shaft 8, which in its end 9 facing away from the loop 7 has a coupling means 10. This means that the loop 7 and the shaft 8 are connectable to and disconnectable from the respective leg 2,3. According to the embodiment shown the coupling means 10 comprises a pin 11 connected with the respective shaft, which is introduceable into a channel 12 formed in the respective leg 2,3. Alternatively, the pin 11 can be connected with the respective leg 2,3, which can be introduced into a channel 12 formed in the shaft. According to another, not shown, embodiment the legs can be equipped with a tube in which the shaft is introduced during connection.

Preferably, the coupling means 10 on each leg 2,3 is situated near to the joint 4 so that the part of the instrument which is to be left by the organ or the tissue, which is to be gripped, shall be as small as possible.

According to FIG. 2, a first embodiment of a locking means 13 is placed on the respective leg 2,3 between the joint 4 and the coupling means 10. The locking means 13 is intended to lock the legs 2,3 tightly so that they cannot rotate in relation to each other, in a gripping position for the instrument 1, for example when the jaw-like leg parts 2,3 have been closed with force around the gripped tissue. The locking means 13 according to FIG. 2 is formed of a hook 14 placed on one leg 2 and a cavity 15 in the other leg 3, which hook 14 is intended to grip into the cavity 15 in a mutually locked position for the legs 2,3.

FIG. 3 shows a second embodiment of a locking means 13', where one leg can be equipped with a hook 14' and the other leg can be equipped with three teeth 15'. The teeth 15' and the hook 14' are intended to grip each other in the locked position of the legs so that three different locking positions can be achieved.

The locking of the legs 2,3 takes place automatically when the shafts 8 and the loops 7 are moved in a direction towards each other. Unlocking takes place through the hook 14,14' and the cavity 15/teeth 15' being moved away from each other by the help of an inclinely directed force of the loops 7. Locking and unlocking of such locking means 13,13' are present on known instruments such as shown in FIG. 1. FIG. 4 shows how a surgical instrument 1 according to the present invention is used. The surgical instrument 1 is introduced through an opening 16 into a body 17, e.g. the abdomen of a person. Inside the body 17 the jaw-like legs 2,3 are clamped fast around an organ 18 by means of hand force through the loops 7 being moved in a direction towards each other. In the clamped position the legs 2,3 are locked by means of the locking means 13,13'. Subsequently the loops 7 and the shafts 8 are disconnected from the legs 2,3 by means of the coupling means 10 and removed out of the opening 16. Other instruments can now be introduced through the opening 16.

The surgical instrument 1 can be made from metal or plastic and as single-use or multiuse instruments. The metal or plastic material must have the characteristic during bending with force to attempt to return to its original shape. The bending energy which is transmitted to the material is moved through the locking means 13,13' to the jaw-like legs 2,3, which then close tight around the gripped tissue. The jaws can be made in any optional length which is determined by the position of the joint 4 in relation to the middle point and the length of the legs 2,3.

I claim:

1. Surgical instrument for laparoscopy comprising two legs (2,3) pivotably joined with each other by means of a joint (4), which legs on a first side of the joint (4) have gripping surfaces (5) facing towards each other and on another side of the joint are equipped each with a handgrip (6) and locking means (13,13'), by means of which the legs (2,3) are lockable with each other, each handgrip (6) having an elongated shaft (8), and coupling means (10) by which each shaft is connectable to and disconnectable from the respective leg (2,3).

2. Instrument according to claim 1, characterized in that respective handgrip (6) is equipped with a shaft (8), which has coupling means (10) in its end (9) facing away from the handgrip (6).

3. Instrument according to claim 2, characterized in that the coupling means (10) comprises a pin (11) connected to the respective shaft (8), which pin is introducible in a channel (12) formed in the respective leg (2,3), or vice versa.

4. Instrument according to claim 1, characterized in that the coupling means (10) of the respective leg (2,3) is situated near to the joint (4).

5. Instrument according to claim 1, characterized in that the locking means (13,13') is a hook (14,14') placed on one leg (2) and a cavity (15) or teeth (15') on the other leg (2), which hook is intended to gip into the cavity (15) or on the teeth (15') in a mutually locked position between the legs (2,3).

6. Instrument according to claim 1, characterized in that the handgrip (6) comprises a loop (7) intended to receive a finger.

7. Instrument according to claim 1, characterized in that the gripping surfaces (5) are flat and equipped with corrugations.

8. Surgical instrument for laparoscopy comprising two legs (2,3) pivotably joined to each other by means of a joint (4), said legs on a first side of the joint (4) having gripping surfaces (5) facing toward each other and on the side of the joint opposite said gripping surfaces (5) each leg having a handgrip (6), locking means on the legs engageable with each other releasably to lock the legs with the gripping surfaces (5) in closed position, said gripping means being disposed between said joint and said handgrips, and a releasable connection on each leg between said locking means and said handgrip, by which the portion of each said leg bearing said handgrip can be detached from the portion of each said leg bearing said releasing connection.

9. Instrument according to claim 8, wherein each said releasable connection is substantially closer to said joint (4) than to said handgrip (6).

* * * * *

UNITED STATES PATENT AND TRADEMARK OFFICE
CERTIFICATE OF CORRECTION

PATENT NO.     : 6,066,159
DATED          : May 23, 2000
INVENTOR(S)    : Bo Bergstrom Page 1 of 1

It is certified that error appears in the above-identified patent and that said Letters Patent is hereby corrected as shown below:

<u>Title page,</u>
Insert Item [30] as follows:

-- [30]     Foreign Application Priority Data
December 7, 1995      [SE]    Sweden.........9504388-1 --.

Signed and Sealed this

Fifth Day of March, 2002

Attest:

JAMES E. ROGAN
*Attesting Officer*     *Director of the United States Patent and Trademark Office*